(12) United States Patent
Hori

(10) Patent No.: US 9,693,740 B2
(45) Date of Patent: Jul. 4, 2017

(54) MEDICAL DIAGNOSTIC IMAGING APPARATUS

(71) Applicant: Hiroshi Hori, Nasushiobara (JP)

(72) Inventor: Hiroshi Hori, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 155 days.

(21) Appl. No.: 13/731,386

(22) Filed: Dec. 31, 2012

(65) Prior Publication Data

US 2014/0051964 A1    Feb. 20, 2014

Related U.S. Application Data

(63) Continuation of application No. PCT/JP2012/070936, filed on Aug. 17, 2012.

(30) Foreign Application Priority Data

Aug. 24, 2011    (JP) ................. 2011-182265

(51) Int. Cl.
*A61B 5/05* (2006.01)
*A61B 6/04* (2006.01)
(Continued)

(52) U.S. Cl.
CPC .......... *A61B 6/0407* (2013.01); *A61B 5/0555* (2013.01); *A61B 6/0457* (2013.01); *A61B 6/035* (2013.01); *A61B 6/037* (2013.01)

(58) Field of Classification Search
CPC .......... A61B 8/00; A61B 6/04; A61B 5/0555; A61B 5/05; A61B 6/0407; A61B 6/0457
(Continued)

(56) References Cited

U.S. PATENT DOCUMENTS

| 7,545,911 B2 * | 6/2009 | Rietzel ............... A61B 6/04 378/205 |
| 2002/0104163 A1 | 8/2002 | Reimann |
| 2007/0003021 A1 * | 1/2007 | Guertin et al. ............... 378/208 |

FOREIGN PATENT DOCUMENTS

| JP | 59-105443 A | 6/1984 |
| JP | 05-317306 A | 12/1993 |

(Continued)

OTHER PUBLICATIONS

International Search Report and Written Opinion issued Sep. 11, 2012 in PCT/JP2012/070936 with English translation of categories of cited documents.

(Continued)

*Primary Examiner* — Joel Lamprecht
(74) *Attorney, Agent, or Firm* — Oblon, McClelland, Maier & Neustadt, L.L.P.

(57) ABSTRACT

A medical diagnostic imaging apparatus includes: a bed device on which an examinee lies down; a gantry having a tunnel-shaped inner portion into which the bed device moves and inserts a table with which the examinee is in direct contact, and being configured to obtain information on an interior of the examinee by imaging the examinee located in the inner portion; and a control device configured to control drive of the bed device and the gantry. The medical diagnostic imaging apparatus further includes a multi-degree-of-freedom support mechanism mounted at a position facing the bed device with the gantry interposed in between and configured to support the table based on a control by the control device in accordance with movement of the table.

28 Claims, 9 Drawing Sheets

(51) Int. Cl.
*A61B 5/055* (2006.01)
*A61B 6/03* (2006.01)

(58) Field of Classification Search
USPC ......... 600/407; 378/62, 63, 208; 5/3, 20, 47, 5/83.1, 601, 607, 612
See application file for complete search history.

(56) References Cited

FOREIGN PATENT DOCUMENTS

| | | |
|---|---|---|
| JP | 09-056711 A | 3/1997 |
| JP | 09-187453 A | 7/1997 |
| JP | 2002-597 A | 1/2002 |
| JP | 2002-253533 A | 9/2002 |
| JP | 2007-167408 A | 7/2007 |
| JP | 2008-142353 A | 6/2008 |
| JP | 2011-55954 A | 3/2011 |

OTHER PUBLICATIONS

Combined Chinese Office Action and Search Report issued Jul. 29, 2014 in Chinese Patent Application No. 201280002538.5 with Japanese translation and English Translation of Category of Cited Documents.

* cited by examiner

MEDICAL DIAGNOSTIC IMAGING APPARATUS

CROSS-REFERENCE TO THE RELATED APPLICATION

This application is based on and claims the benefit of priority from Japanese Patent Application No. 2011-182265, filed on 24 Aug. 2011; the entire contents of which are incorporated herein by reference.

FIELD

Embodiments relate to a table for CT imaging and an X-ray CT apparatus, and for example to a table for CT imaging and an X-ray CT apparatus equipped with an aid for holding part of an examinee.

BACKGROUND

Medical diagnostic imaging apparatuses configured to collect information on the interior of an examinee, and to create a medical image by generating an image of the interior of the examinee based on the collected information have been used in recent years. Such medical diagnostic imaging apparatuses include, for example, an X-ray CT (computed tomography) apparatus, a magnetic resonance imaging (MRI) apparatus, a PET (positron-emission tomography) apparatus, and the like.

In order to be able to successively collect information on the interior of the entire body of an examinee, these medical diagnosis apparatus are configured such that a table on which an examinee lies down can slide from a bed device toward a gantry by, for example, about 2000 mm. However, this table is often supported only by the bed device. Accordingly, as the table slides more, the height of an unsupported end of the table might become lower than the height of the other end of the table which is supported by the bed device, in other words, the table might bow. Such bowing of the table causes a shift of the vertical center at a scan point. This shift largely affects the quality of an image obtained.

The invention described in Japanese Patent Application Publication No. Hei 5-317306 copes with such a shift by increasing the positions at which the table is supported. Further, the invention described in Japanese Patent Application Publication No. Hei 9-056711 copes with the shift by providing a support member inside the tunnel-shaped gantry at a position where the table exits from the inside of the gantry.

Although the inventions described in Japanese Patent Application Publications Nos. Hei 5-317306 and Hei 9-056711 are both provided with a support portion for the table in addition to the bed device, the support portion is provided at a position after the exit where the table exits from the inside of the gantry. Accordingly, the table still has to be supported by the bed device until that position, and it is difficult to solve the problem of the bowing of the table (shift in the image) at the scan point inside the gantry (such a point is called an "X-ray path" below). A conceivable method for solving the bowing of the table with such a configuration is, for example, to enhance the strength of the table by increasing the thickness of the table.

To perform imaging to obtain interior information on an organ, such as a heart, which is offset from the body axis of an examinee, the table enters the inside of the gantry while being shifted in the width direction of the examinee according to the position to be imaged. To support the table in such a case, a support mechanism has to have a large structure, and this might be unfavorable in view of the installation space and operability.

DETAILED DESCRIPTION

According to one embodiment, a medical diagnostic imaging apparatus comprises: a bed device on which an examinee lies down; a gantry having a tunnel-shaped inner portion into which the bed device moves and inserts a table with which the examinee is in direct contact, and being configured to obtain information on an interior of the examinee by imaging the examinee located in the inner portion; and a control device configured to control drive of the bed device and the gantry. The medical diagnostic imaging apparatus further comprises a multi-degree-of-freedom support mechanism installed at a position facing the bed device with the gantry in between and configured to support the table based on a control by the control device in accordance with movement of the table.

Embodiments of the present invention are described in detail below with reference to the drawings.

Figure 1:
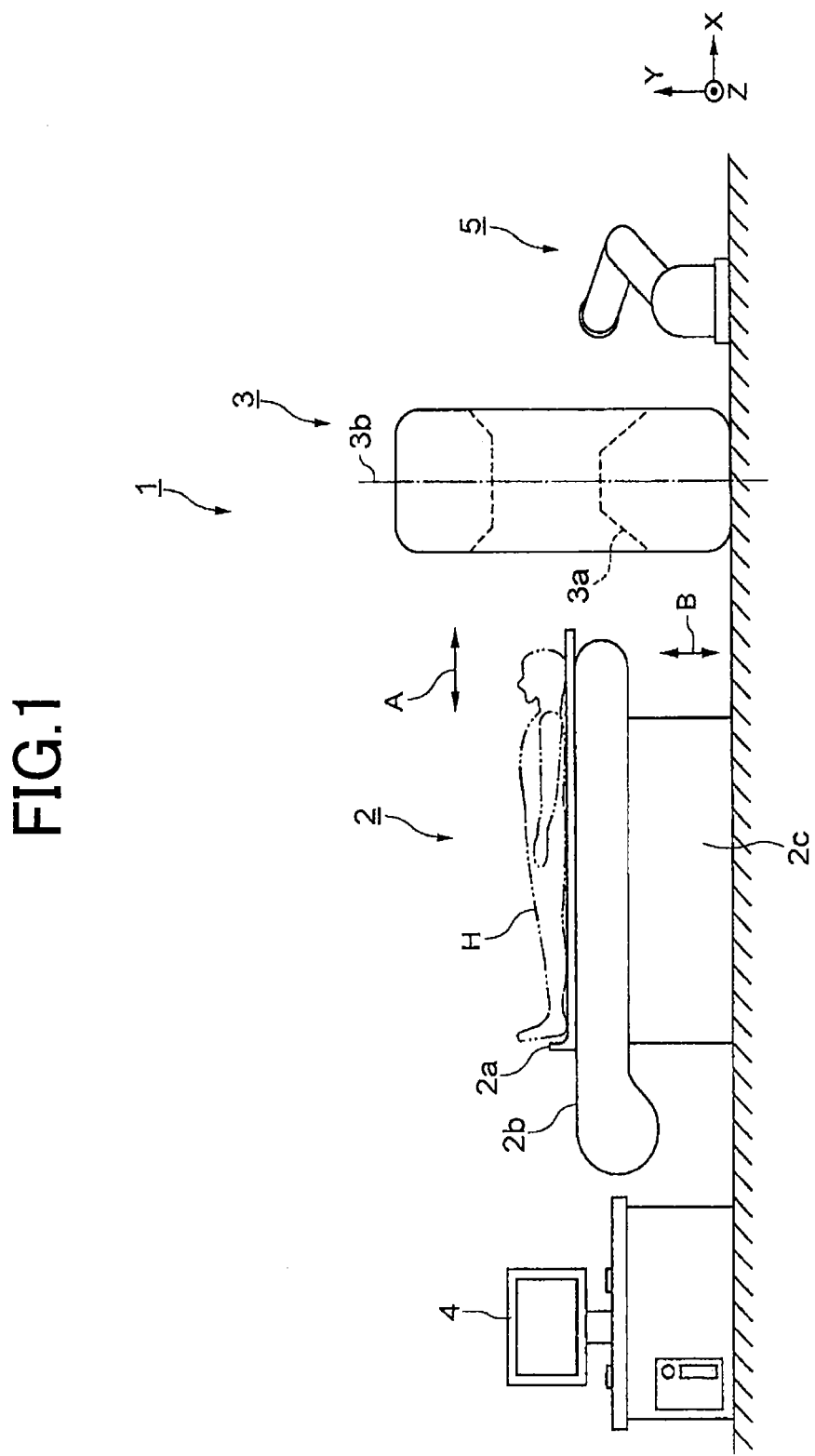
FIG. 1 is an overview showing the overall configuration of a medical diagnostic imaging apparatus according to an embodiment of the present invention.

FIG. 1 is an overview showing the overall configuration of a medical diagnostic imaging apparatus 1 according to an embodiment of the present invention. The medical diagnostic imaging apparatus 1 includes a bed device 2 having a table 2a on which an examinee H lies down, a gantry 3, and a control device 4 configured to control the medical diagnostic imaging apparatus 1. The medical diagnostic imaging apparatus 1 according to the embodiment of the present invention further includes a multi-degree-of-freedom table support mechanism 5 installed at a position facing the bed device 2 with the gantry 3 interposed in between and configured to support the table 2a in accordance with the movement of the table 2a.

Descriptions of the embodiment of the present invention assume that the control device 4 is provided as a console as shown in FIG. 1 for example, and that the medical diagnostic imaging apparatus 1 is controlled based on signals from the control device 4. Alternatively, functions of the control device may be provided to the gantry 3 so that the control device of the gantry 3 performs overall control of the medical diagnostic imaging apparatus 1.

Further, the medical diagnostic imaging apparatus 1 may be an X-ray CT apparatus, a magnetic resonance imaging (MRI) apparatus, a PET (positron-emission tomography) apparatus, or any other type as long as it images the examinee H lying down on the table 2a of the bed device 2 which has entered the inside of the apparatus (the gantry). Note that an X-ray CT apparatus is used as an example below, when appropriate.

The bed device 2 includes the table 2a, a bed 2b configured to support the table 2a, and a base 2c configured to support the table 2a and the bed 2b. When the medical diagnostic imaging apparatus 1 is used to acquire information on the interior of the examinee H, i.e., to image the examinee H, the examinee H is in direct contact with (lies down on) the table 2a. Note that the shape of the cross section of the table 2a along its short axis may be horizontal or curved to the examinee H lying down thereon. The table 2a can advance and retreat in both directions (horizontal direction) indicated by arrows A shown in FIG. 1 so that the examinee H lying down thereon can be imaged inside the gantry 3.

The bed 2b supports the table 2a. Various devices are provided inside the bed 2b, including a drive device configured to drive the table 2a when the table 2a is to move in the directions indicated by arrows A, an encoder configured to measure the tilt of the table 2a caused when the table 2a moves, and the like. Measurement results obtained by these various devices are sent to the control device 4. Note that when the table 2a moves in the directions of arrows A, the bed 2b does not move. Accordingly, for example, the position where the bed 2b supports the table 2a when the table 2a moves toward the gantry 3 is, if shown by the body part, the entire examinee H at the start of the movement, and then shifts, along with the movement, to the chest, the torso, the legs, the torso, the legs, and the legs.

The base 2c supports the table 2a and the bed 2b. The base 2c is movable in the vertical direction, namely, the directions indicated by arrows B shown in FIG. 1 so as to be able to adjust the height at which the examinee H and the table 2a enter the gantry 3. Like the bed 2b, the base 2c does not move even when the table 2a moves.

The gantry 3 is configured to irradiate the examinee H with X rays in an example of an X-ray CT apparatus. To allow the examinee H (the table 2a) to enter and retreat, the gantry 3 is provided with a tunnel-shaped opening 3a at its center. The gantry 3 houses an X-ray irradiator (not shown) (e.g., an X-ray tube) and a light receiving element (not shown) (e.g., an X-ray detector). The X-ray irradiator and the light receiving element image the examinee H while rotating therearound. The table 2a on which the examinee H is lying down moves by a necessary distance in the directions of arrows A in accordance with the progress of the imaging by the gantry 3. Note that the position at which the examinee H is irradiated with X rays in the gantry 3 (an imaging position) is called an "X-ray path" and is indicated by chain line 3b in FIG. 1. The gantry 3 can tilt toward the bed device 2 or a multi-degree-of-freedom support mechanism 5 to be described later, according to the mode of imaging.

The control device 4 is configured as a console in the embodiment of the present invention, as shown in FIG. 1. The console (the control device 4) is arranged side-by-side with the bed device 2 and the gantry 3 in FIG. 1, but may be provided in a room different from the examination room where the bed device 2 and the gantry 3 are installed. To carry out imaging of the examinee H, for example, the technologist operates the console (the control device 4), and drive of the medical diagnostic imaging apparatus 1 (the bed device 2, the gantry 3, and the multi-degree-of-freedom support mechanism 5) is controlled based on control signals generated.

Figure 2:
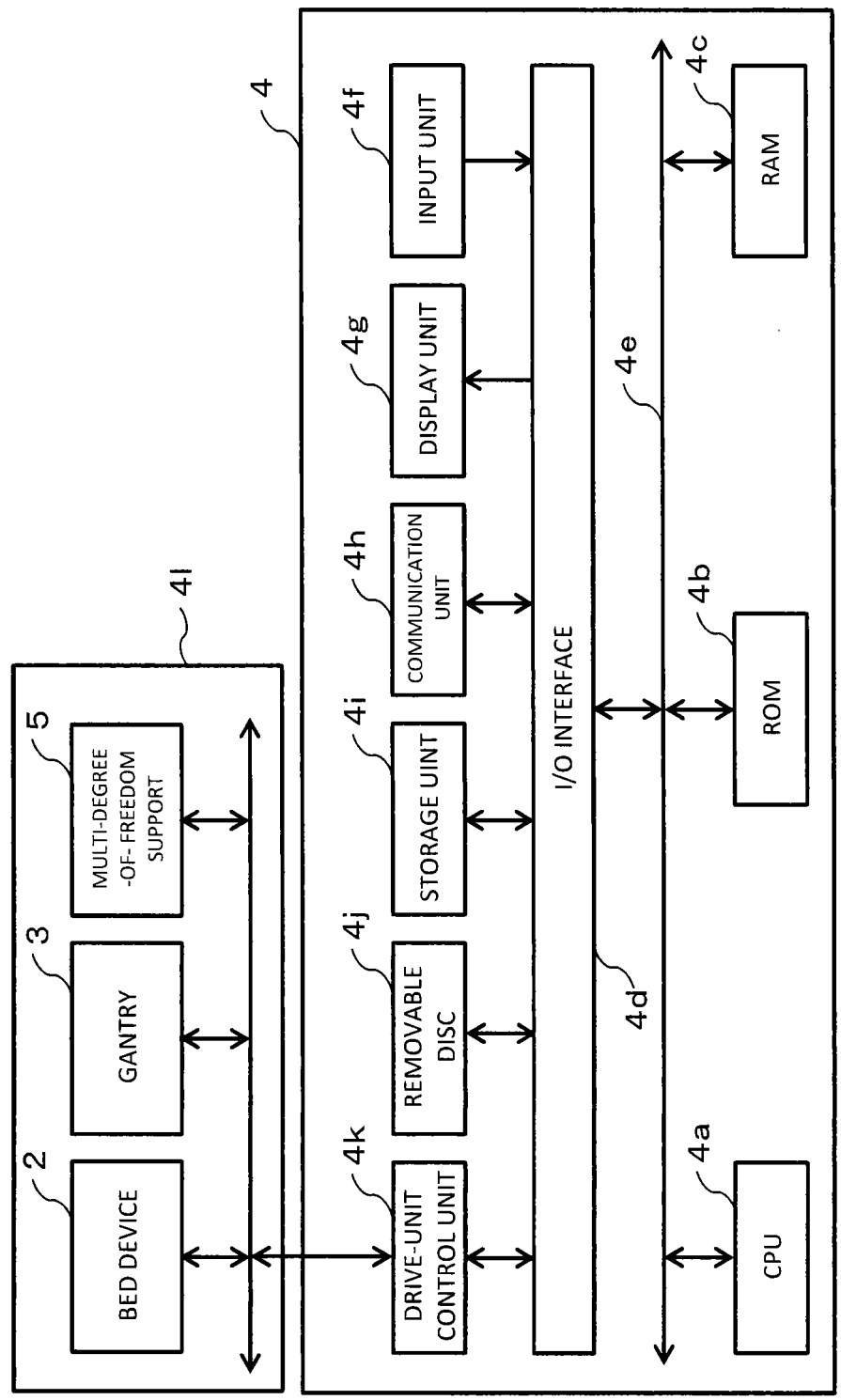
FIG. 2 is a block diagram showing the internal configuration of a control device of the medical diagnostic imaging apparatus according to the embodiment of the present invention.

FIG. 2 is a block diagram showing the internal configuration of the control device 4 of the medical diagnostic imaging apparatus 1 according to the embodiment of the present invention.

In the control device 4, a CPU (Central Processing Unit) 4a, a ROM (Read Only Memory) 4b, a RAM (Random Access Memory) 4c, and an I/O interface 4d are connected to one another via a bus 4e. The I/O interface 4d is connected to an input unit 4f, a display unit 4g, a communication control unit 4h, a storage unit 4i, a removable disc 4j, and a driving-unit control unit 4k. For example, the driving-unit control unit 4k controls a driving unit 4l of the medical diagnostic imaging apparatus 1, the driving unit 4l unit including the bed device 2, the gantry 3, and the multi-degree-of-freedom support mechanism 5.

Based on an input signal from the input unit 4f, the CPU 4a reads a boot program, from the ROM 4b, for activating the medical diagnostic imaging apparatus 1, executes the boot program, and reads an operating system stored in the storage unit 4i. Via the input unit 4f and the I/O interface 4d, the CPU 4a also controls various devises based on input signals from other external devices not shown in FIG. 1.

Further, the CPU 4a reads programs and data stored in the RAM 4c, the storage unit 4i, and the like and load them to the RAM 4c. Moreover, the CPU 4a is a processor configured to implement a series of processes, such as drive control processing of each unit, calculation and process of data, and the like, based on commands of the programs read out from the RAM 4c.

The input unit 4f is configured with an input device, such as a keyboard or a dial, with which the operator (e.g., a doctor or a technologist) of the medical diagnostic imaging apparatus 1 inputs various operations. The input unit 4f generates an input signal based on the operation made by the operator, and sends the input signal to the CPU 4a via the bus 4e.

The display unit 4g is, for example, a liquid crystal display as shown in FIG. 1. The display unit 4g receives an output signal from the CPU 4a via the bus 4e, and displays an image or the like necessary for setting conditions used in, for example, imaging or image processing, a processing result of the CPU 4a, or the like.

The communication control unit 4h is means, such as a LAN card or a modem, capable of connecting the medical diagnostic imaging apparatus 1 to a communication network such as the Internet or a LAN. Data exchanged through the communication network via the communication control unit 4h are sent to and received from the CPU 4a via the I/O interface 4d and the bus 4e, as an input signal or an output signal.

The storage unit 4i is configured of a semiconductor or a magnetic disc, and stores programs executed by the CPU 4a and data.

The removable disc 4j is an optical disc or a flexible disc, and signals read or written by a disc drive are sent to and received from the CPU 4a via the I/O interface 4d and the bus 4e.

The multi-degree-of-freedom support mechanism 5 shown in FIG. 1 is a mechanism configured to support the table 2a so that the table 2a entering the gantry 3 will not flex due to the weight of the examinee H to be imaged. Although the multi-degree-of-freedom support mechanism 5 is shown in FIG. 1, this is just an example. Any mechanism may be employed as long as it can play the above-described function of the multi-degree-of-freedom support mechanism 5.

Figure 3:
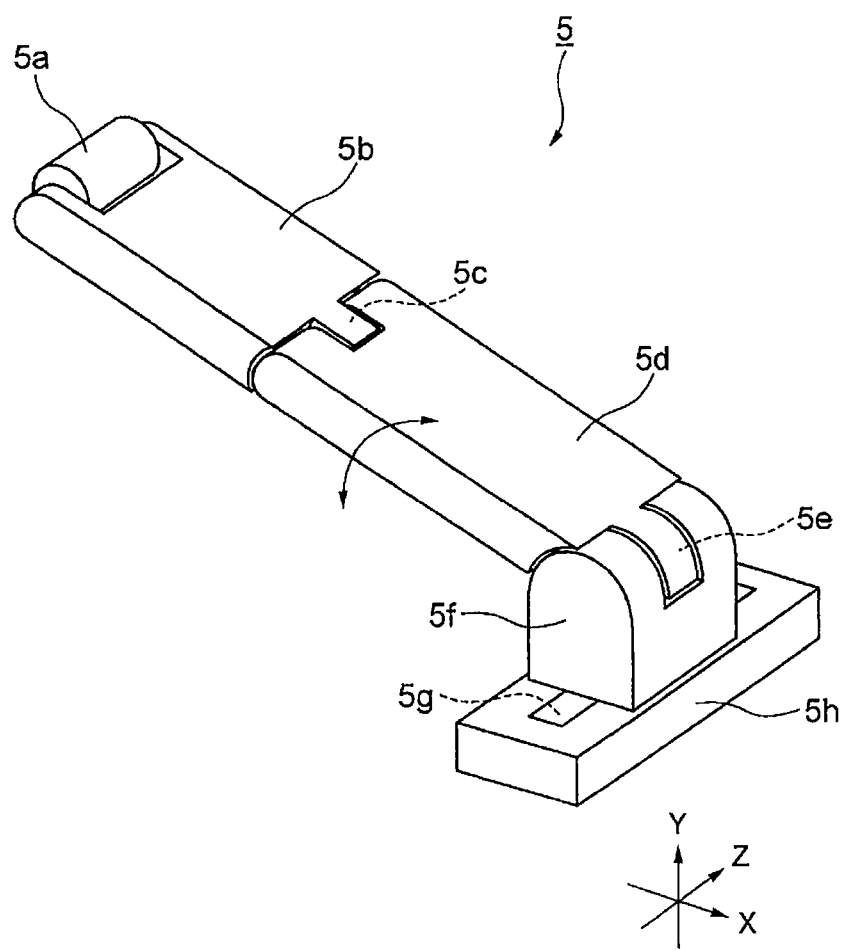
FIG. 3 is a perspective view showing the overall configuration of the medical diagnostic imaging apparatus according to the embodiment of the present invention.

FIG. 3 is a perspective view showing the overall configuration of the multi-degree-of-freedom support mechanism 5 according to the embodiment of the present invention.

The multi-degree-of-freedom support mechanism 5 includes a table support portion 5a configured to support the table 2a by coming into direct contact with it, a first arm 5b configured to movably support, at its one end (a first end), the table support portion 5a, and a first connection portion 5c being the other end (a second end) of the first arm 5b and configured to rotatably support the first arm 5b. The multi-degree-of-freedom support mechanism 5 further includes a second arm 5d connected at one end (a first end) to the first connection portion 5c and thereby connected to the first arm 5b, and a second connection portion 5e being the other end (a second end) of the second arm 5d and configured to rotatably support the second arm 5d. The multi-degree-of-freedom support mechanism 5 further includes a third arm 5f connected at one end (a first end) to the second connection portion 5e and thereby connected to the second arm 5d, a third connection portion 5g being the other end (a second end) of the third arm 5f and configured to movably support the third arm 5f, and an installation portion 5h securing the multi-degree-of-freedom support mechanism 5 to an installation surface.

As shown in FIGS. 8 to 11 to be described later, the table support portion 5a comes into direct contact with the table 2a and supports the table 2a. For example, the table support portion 5a is configured to be rotatable in the moving directions of the table 2a so as not to hinder the movement of the table 2a moving while being in contact with the table support portion 5a. Alternatively, the table support portion 5a may be configured to be able to hold a longitudinal end portion of the table 2a. Still alternatively, the table support portion 5a may be configured to be able to be fitted onto a protrusion provided to the back side of the table 2a (the surface not in contact with the examinee H).

The first arm 5b has the table support portion 5a at its one end (a first end) and has the first connection portion 5c at the other end (a second end). When the first connection portion 5c moves rotatably, the first arm 5b, too, moves with the first connection portion 5c as the center of rotation. When the first arm 5b moves, the table support portion 5a provided to one end of (a first end) the first arm 5b moves as well.

Although not shown in FIG. 1, a power source, such as a motor, configured to drive the first arm 5b is placed inside the first connection portion 5c, and the second connection portion 5e (the second arm 5d) is rotatable by being driven by the power source. An encoder configured to measure the tilt of the first arm 5b is also placed inside the first connection portion 5c. The power source and the encoder are connected to the control device 4, to drive the first arm 5b according to the command by the control device 4 and to send the control device 4 information on the movement of the first arm 5b. The first connection portion 5c has substantially the same configuration as the second connection portion 5e, and will therefore be described together with the second connection portion 5e later.

The second arm 5d is connected at one end (a first end) to the first connection portion 5c and at the other end (a second end) to the second connection portion 5e. The movement of the second connection portion 5e restricts the movement of the second arm 5d as well as the movements of the first connection portion 5c, the first arm 5b, and the table support portion 5a which are connected to the end (a first end) of the second arm 5d directly and indirectly.

Although not shown in FIG. 1, a power source, such as a motor, configured to drive the second arm 5d is placed inside the second connection portion 5e, and the second connection portion 5e (the second arm 5d) is rotatable by being driven by the power source. An encoder configured to measure the tilt of the second arm 5d is also placed inside the second connection portion 5e. The power source and the encoder are connected to the control device 4, to drive the second arm 5d according to the command by the control device 4 and to send the control device 4 information on the movement of the second arm 5d.

Figure 4:
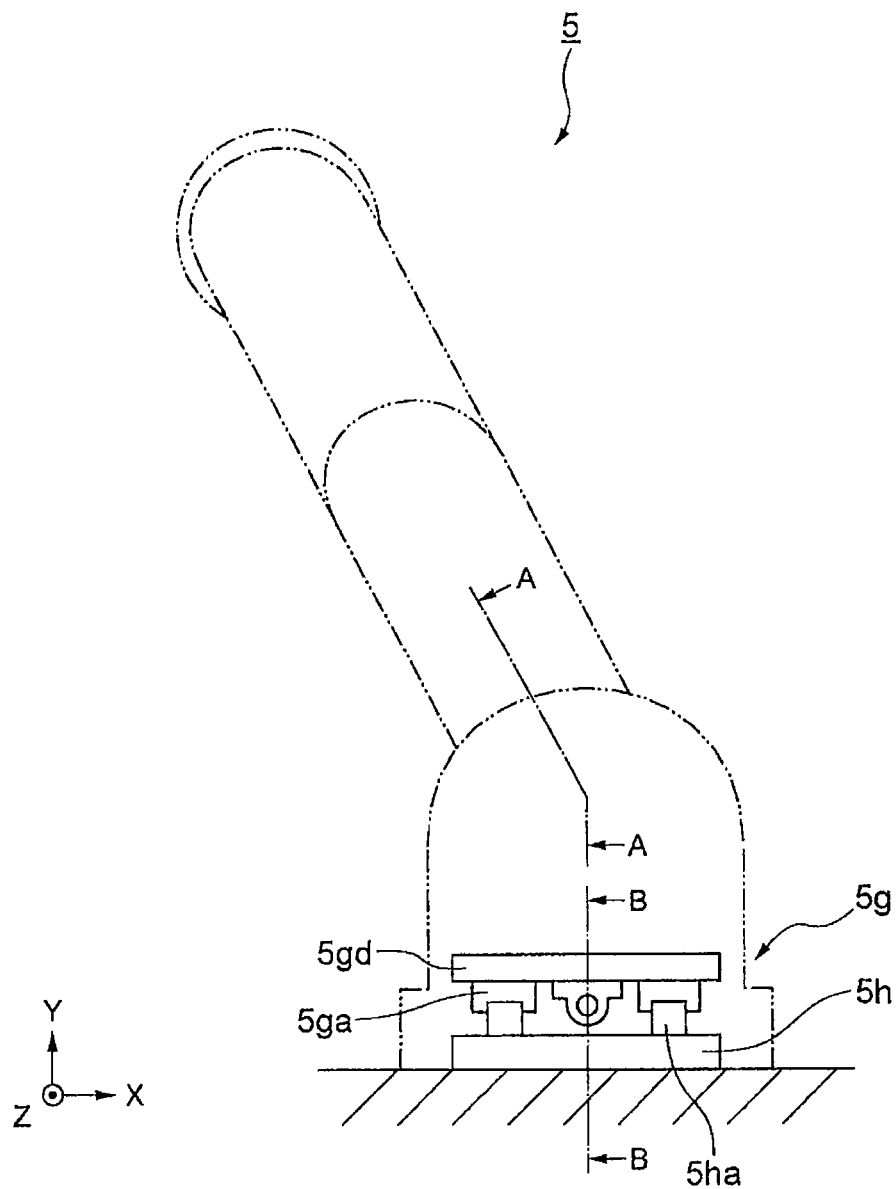
FIG. 4 is an explanatory diagram showing the multi-degree-of-freedom support mechanism including a third connection portion, in the Z-axis direction shown in FIG. 1.
Figure 5:
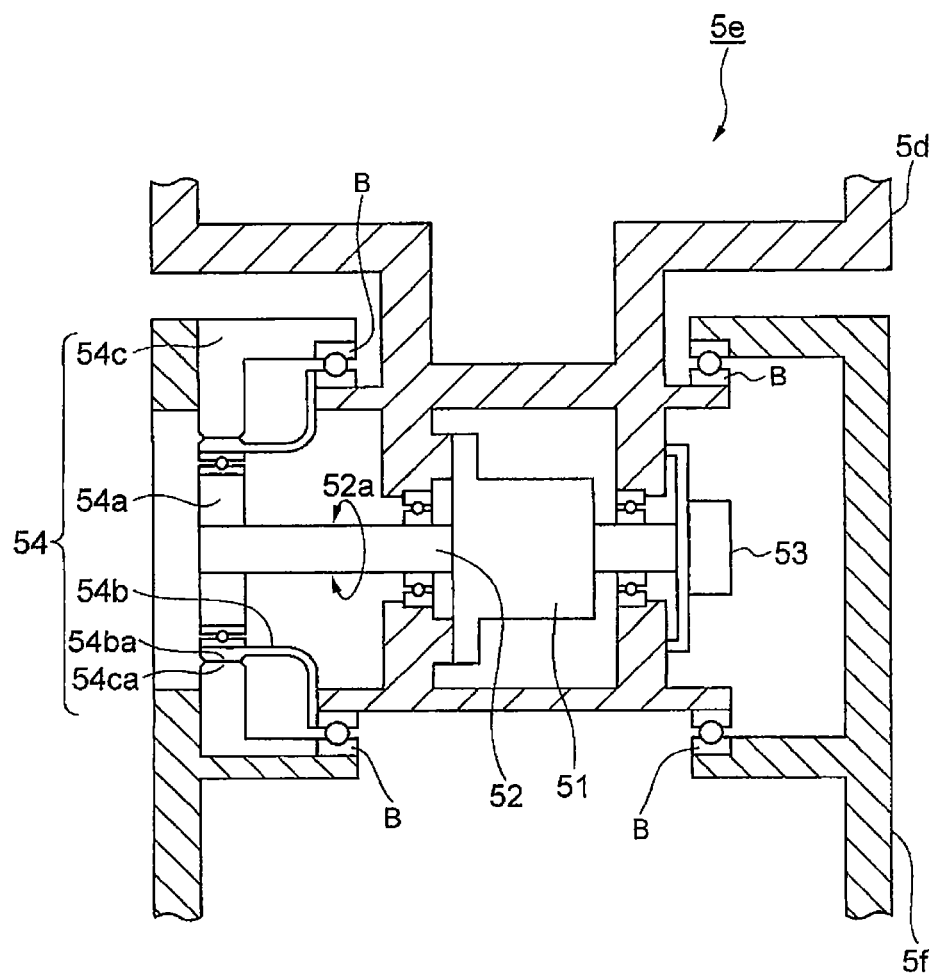
FIG. 5 is a sectional view on line A-A in FIG. 4.

FIG. 4 is an explanatory diagram showing the multi-degree-of-freedom support mechanism 5 including the third connection portion 5g, seen in the Z-axis direction shown in FIG. 1. FIG. 5 is a sectional view taken along line A-A in FIG. 4. This sectional view taken along line A-A shows a section of the second connection portion 5e. The second arm 5d is cut off at the upper part of FIG. 5 to show only its joint portion. A motor 51 which is the power source described above is placed at the center part. In other words, in FIG. 5, the other end (a second end) of the second arm 5d is formed into a projection shape, and the motor 51 is housed in this projecting portion of the second arm 5d. The third arm 5f is connected to the second arm 5d via ball bearings B while surrounding the motor 51. The second arm 5d and the third arm 5f are connected to each other in this way. Accordingly, the second arm 5d can move in arrowed directions shown in FIG. 3 when drive of the motor 51 is transmitted to the second arm 5d via a drive transmission device to be described later.

A rotation shaft 52 penetrates the center of the motor 51 in the Z-axis direction. An encoder 53 is connected to one end of the rotation shaft 52 to be able to measure tilt of the second arm 5d based on the number of rotations of the rotation shaft 52.

A drive transmission device 54, such as a harmonic drive (registered trademark), is attached to the other end of the rotation shaft 52. In FIG. 5, the drive transmission device 54 is shown to have top-bottom symmetry with respect to the rotation shaft 52.

The drive transmission device 54 according to the embodiment of the present invention includes a wave generator 54a connected directly to the rotation shaft 52, a flex spline 54b, and a circular spline 54c. The wave generator 54a employs a configuration of an oval cam with a ball bearing mounted on its outer circumference. The inner race in contact with the ball bearing is a cam and therefore does not deform, but the outer race in contact with the ball bearing elastically deforms according to the movement of the ball bearing which follows the movement of the cam. Accordingly, when the wave generator 54a rotates, the outer race flexes into an eclipse shape.

When the motor 51 rotates to rotate the rotation shaft 52 in any of the directions indicated by arrows 52a, the wave generator 54a connected to the rotation shaft 52, too, rotates in that rotation direction. The rotation of the wave generator 54a causes the flex spline 54b to flex into an eclipse shape, and teeth 54ba of the flex spline 54b mesh with teeth 54ca of the circular spline 54c which is an output ring. As a result, the second arm 5d rotates since the circular spline 54c is fixed to the third arm 5f.

Although the harmonic drive (registered trademark) is used herein as an example of the drive transmission device 54, any type of drive transmission device may be used.

In sum, when the motor 51 is driven, the rotation shaft 52 rotates in either of the directions of arrows 52a. Then, the drive transmission device 54 gives the second arm 5d the drive force of the motor 51, and thus the second arm 5d is allowed to rotate in an instructed direction.

The third arm 5f is connected at one end (a first end) to the second connection portion 5e and at the other end (a second end) to the third connection portion 5g. The movement of the third connection portion 5g restricts not only the movement of the third connection portion 5g, but also the overall movement of the multi-degree-of-freedom support mechanism 5.

Although not shown in FIG. 1, a power source, such as a motor, configured to drive the third arm 5f is placed inside the third connection portion 5g, and thus the third connection portion 5g is allowed to move. The power source is connected to the control device 4 to drive the third arm 5f according to the command by the control device 4 and to send the control device 4 information on the movement of the third arm 5f.

Figure 6:
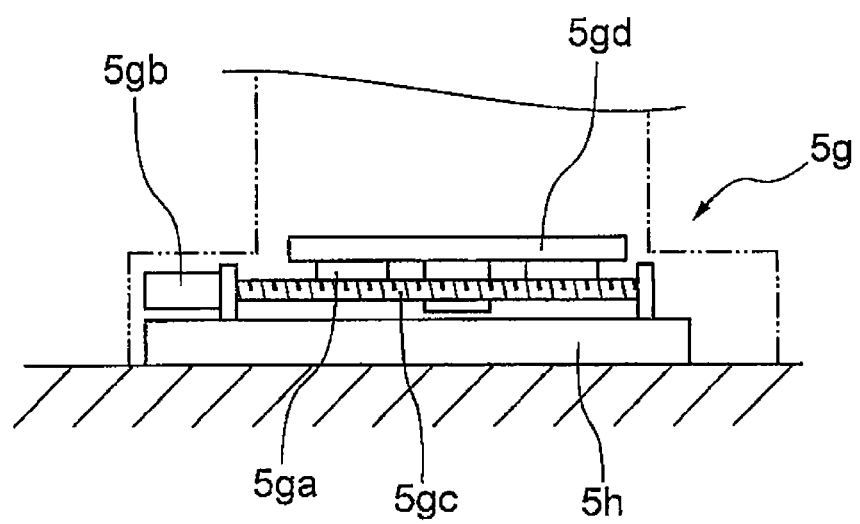
FIG. 6 is a sectional view on line B-B in FIG. 4.

FIG. 6 is a sectional view taken along line B-B in FIG. 4. In this sectional view on line B-B, the third connection portion 5g is sectioned and seen in the same direction as in FIG. 5. The third connection portion 5g includes LM guides 5ga movable in the Z-axis direction by gripping guide rails 5ha placed on the installation portion 5h, and a motor 5gb. The motor 5gb allows the third arm 5f, the second connection portion 5e, the second arm 5d, the first connection portion 5c, the first arm 5b, and the table support portion 5a to move in the Z-axis direction. To be more specific, when the motor 5gb rotates a ball bearing 5gc in either direction, the third connection portion 5g connected and fixed to a connection platform 5gd as well as the rest of the portions up to the table support portion 5a are moved.

Note that the amount of movement of each of the third arm 5b, the second arm 5d, and the third arm 5f are determined by the amount of movement of a corresponding one of the third connection portion 5c, the second connection portion 5e, and the third connection portion 5g, but the actual amount of movement of each arm (or the amount of movement of each connection portion) is determined based on the command by the control device 4.

In addition, the multi-degree-of-freedom support mechanism 5 according to the embodiment of the present invention is allowed to move in the Z-axis direction owing to the above-described configuration of the third connection portion 5g. This is because, depending on the imaging of the examinee H, the table 2a (the examinee H) might need to be moved in the width direction of the gantry 3 (the Z direction) with respect to the body axis of the examinee H. By being configured to be movable in this way, the multi-degree-of-freedom support mechanism 5 can support the table 2a no matter what the imaging mode is.

The installation portion 5h is configured to secure the multi-degree-of-freedom support mechanism 5 to the installation surface. Here, the "installation surface" indicates the surface on which the multi-degree-of-freedom support mechanism 5 is installed, and may be the same surface as a surface on which the other components of the medical diagnostic imaging apparatus 1 are installed.

Note that the installation portion 5h may be configured to secure the multi-degree-of-freedom support mechanism 5 to the installation surface, but not to negate the capability of the installation portion 5h itself to move. Specifically, the installation portion 5h may move on the installation surface according to the movement of the table 2a, to thereby move the multi-degree-of-freedom support mechanism 5 itself.

Figure 7:
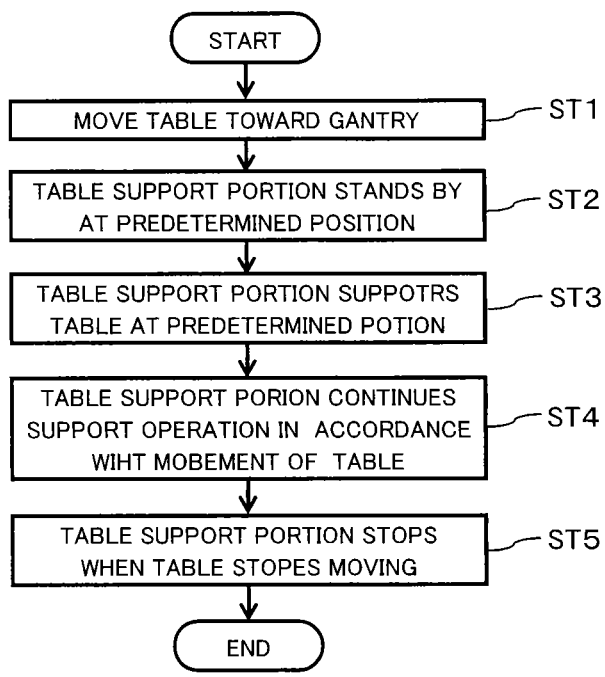
FIG. 7 is a flowchart showing the flow of how the multi-degree-of-freedom support mechanism moves in accordance with the movement of a table.

Next, a description is given of how the multi-degree-of-freedom support mechanism 5 moves according to the movement of the table 2a entering or retreating from the opening 3a of the gantry 3. FIG. 7 is a flowchart showing the flow of how the multi-degree-of-freedom support mechanism 5 moves in accordance with the movement of the table 2a. Further, FIGS. 8 to 11 are explanatory diagrams showing an example of how the multi-degree-of-freedom support mechanism 5 moves in accordance with the table 2a.

First, the examinee H lies down on the table 2a of the bed device 2 (see FIG. 1). To image the examinee H using the medical diagnostic imaging apparatus 1, the table 2a needs to be inserted into (or enter) the inside (opening) 3a of the gantry 3. Therefore, the control device 4 causes the table 2a to move toward the gantry 3 (ST1).

Meanwhile, the multi-degree-of-freedom support mechanism 5 moves the table support portion 5a to a position near the opening 3a which the table 2a enters, and stands by at that position for the table 2a to enter (ST2). In the embodiment of the present invention, the table support portion 5a is moved to, for example, the position near the X-ray path and stands by there. Note that at which position the table support portion 5a should stand by can be decided appropriately.

However, one of the objectives of the present invention is to prevent the table 2a from bowing (flexing) due to the weight of the examinee H lying down on the table 2a during imaging. Accordingly, the table 2a should preferably be supported at as an early stage as possible. For example, at which position the table support portion 5a should stand by for the table 2a may be determined considering factors such as the length of each arm constituting the multi-degree-of-freedom support mechanism 5.

Figure 8:
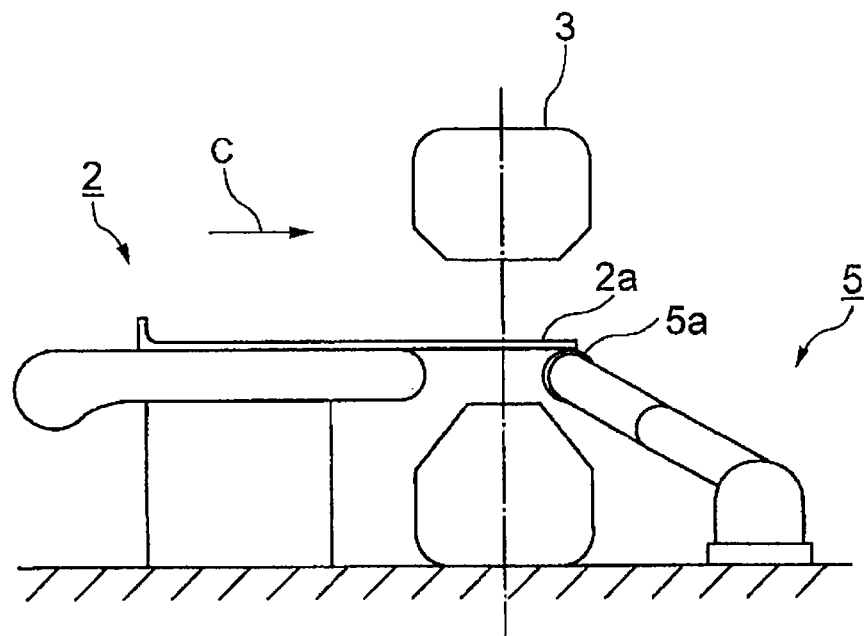
FIG. 8 is an explanatory diagram showing an example of how the multi-degree-of-freedom support mechanism moves in accordance with the movement of the table.

While the table support 5a waits for the table 2a, the table 2a moves to enter the opening 3a of the gantry 3. When the table 2a reaches the standby position of the table support portion 5a, the table support portion 5a comes into contact with the table 2a and thus supports the table 2a (ST3). The explanatory diagram of FIG. 8 shows this state. Note that, for the purpose of easy understanding, the gantry 3 in the diagrams of FIG. 8 and so on is sectioned in the vertical direction, and its end section is shown in a simplified form. In addition, the examinee H is not shown in these diagrams.

As shown in FIG. 8, the table 2a is moving in a direction indicated by arrow C. Meanwhile, as described above in the embodiment of the present invention, the multi-degree-of-freedom support mechanism 5 moves the table support portion 5a to a position near the X-ray path, and the table support portion 5a waits for the table 2a to move. Accordingly, the first arm 5b and the second arm 5d are almost stretched. Then, when the table support portion 5a comes into contact with and thus supports the table 2a, the table 2a is now supported by the bed device 2 and the table support portion 5a (i.e., the multi-degree-of-freedom support mechanism 5).

As the imaging by the gantry 3 progresses, the table 2a gradually enters further inside the opening 3a (moves in the direction of arrow C). Meanwhile, the table support portion 5a continues its support operation while the table 2a is moving (ST4). The control device 4 receives input of information on the tilt of the table 2a via the encoder provided to the bed 2b. Also, the travel distance of the table 2a can be calculated from, for example, the number of rotations of the drive motor of the bed device 2. These pieces of information on the position of the table 2a are sequentially collected by the control device 4. These pieces of information collected by the control device 4 are used to control the movement of the multi-degree-of-freedom support mechanism 5 so that the table 2a can maintain its tilt which it has at the start of imaging, and may not further tilt or flex.

Figure 9:
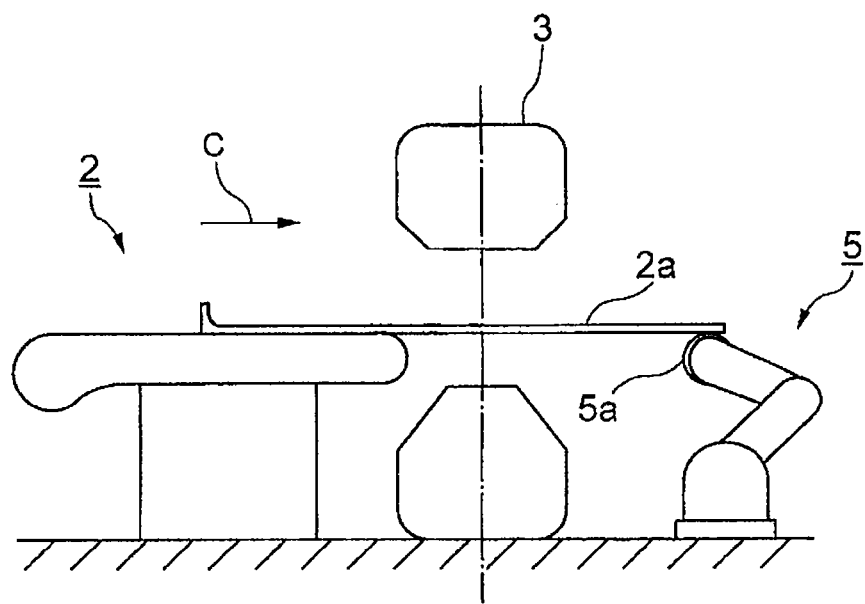
FIG. 9 is an explanatory diagram showing an example of how the multi-degree-of-freedom support mechanism moves in accordance with the movement of the table.

FIG. 9 shows a state where the table 2a has advanced in the direction of arrow C farther than the state shown in FIG. 8. In accordance with the movement of the table 2a, the table support portion 5a also moves in the direction of arrow C without shifting the position in contact with the table 2a.

As the imaging progresses, the table 2a comes out from the opening 3a of the gantry 3 to the side where the multi-degree-of-freedom support mechanism 5 is installed, and stops when reaching a position at which the table 2a has moved farther away from the bed device 2 (such a position is called to an "IN limit position"). In response to this, the multi-degree-of-freedom support mechanism 5 stops moving at the position where the table 2a is stopped (ST5).

Figure 10:
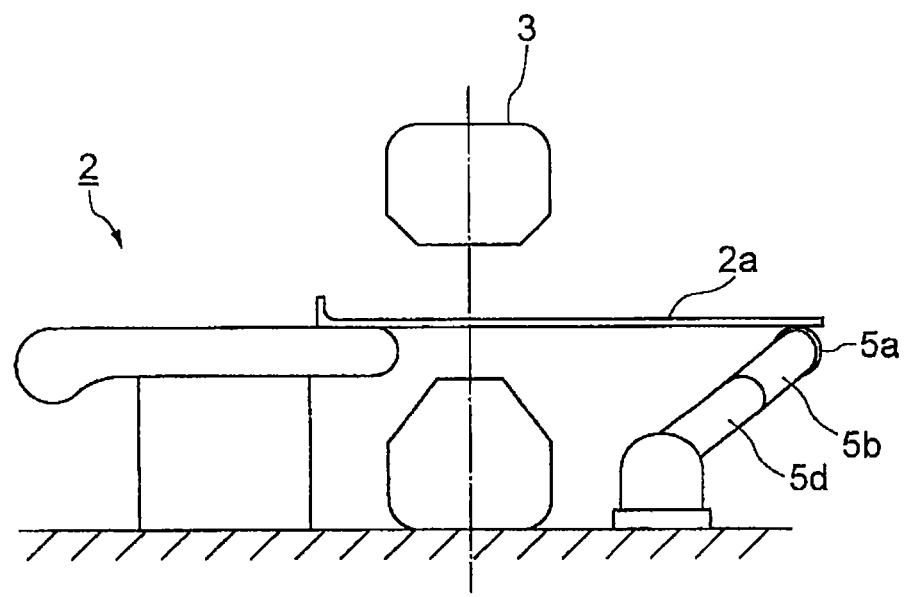
FIG. 10 is an explanatory diagram showing an example of how the multi-degree-of-freedom support mechanism moves in accordance with the movement of the table.

FIG. 10 shows this state. In FIG. 10, the first arm 5b and the second arm 5d of the multi-degree-of-freedom support mechanism 5 are almost stretched out to a direction away from the gantry 3, in contrast to the state where the multi-degree-of-freedom support mechanism 5 waits for the table 2a at the position near the X-ray path (see FIG. 8). This is a result of the table support portion 5a moving in accordance with the table 2a without shifting the position in contact with the table 2a until the table 2a stops.

As described above, by supporting the moving table not only with the bed device but also with the multi-degree-of-freedom table support mechanism, the flexure of the table is suppressed as much as possible to prevent a decrease in the quality of the image obtained. Further, employment of such a mechanism eliminates the necessity of increasing the thickness of the table to prevent the table from flexing. Accordingly, the table can be reduced in thickness, which can contribute to reduction in cost of the medical diagnostic imaging apparatus. Furthermore, the multi-degree-of-freedom support mechanism can follow any movement of the table as described above, and therefore can support the table at any position without concerning about the position of the table.

Accordingly, what can be provided is a medical diagnostic imaging apparatus including a multi-degree-of-freedom support mechanism capable of obtaining a high quality image by preventing flexure of a table across the entire imaging area of an examinee without increasing the thickness of the table, and capable of moving in accordance with the movement of a component device.

Especially when the medical diagnostic imaging apparatus is a CT-PET, conventionally, the gantry or the bed device itself moves in a direction horizontal to the installation surface to prevent flexure of the table. However, the gantry or the like no longer has to move if the above-described multi-degree-of-freedom support mechanism is employed. Thus, the area for installation of the medical diagnostic imaging apparatus (CT-PET) can be minimized (to the projected area of the apparatus).

Even a medical diagnostic imaging apparatus in which the gantry is formed by multiple divided gantries having respective functions can be equipped with the above-described multi-degree-of-freedom support mechanism. In this case, for example, the multi-degree-of-freedom support mechanism may be installed at a position facing the bed device with the multiple gantries interposed in between. Further, when each of these multiple gantries is configured movably, the multi-degree-of-freedom support mechanism may be installed between these multiple gantries. When the multi-degree-of-freedom support mechanism is installed at such a position, the table can be efficiently prevented from flexing while the table enters and exits the multiple gantries sequentially. Further, the multi-degree-of-freedom support mechanism may be mounted at a position facing the bed device with the multiple gantries interposed in between, and also at a position between the multiple gantries.

Figure 11:
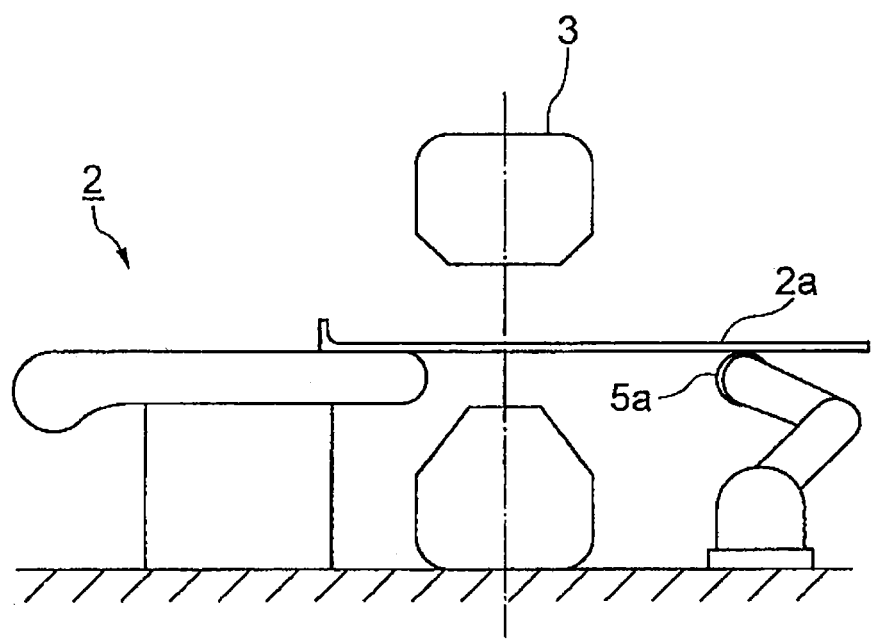
FIG. 11 is an explanatory diagram showing an example of how the multi-degree-of-freedom support mechanism moves in accordance with the movement of the table.

The movement of the multi-degree-of-freedom support mechanism 5 when the table has moved to the IN limit position can be controlled as follows other than as described above. Specifically, for example, instead of following the table 2a to the IN limit position, the multi-degree-of-freedom support mechanism 5 may be controlled not to move from a certain position but to allow the table 2a to move on the table support portion 5a, as shown in FIG. 11. In this case, the table support portion 5a may have a structure allowing the table 2a to slide thereon, or a structure rotatable in the moving direction of the table 2a.

In this case, the table support portion 5a supports the table 2a at a position closer to the bed device 2. Accordingly, in addition to offering the above described effects, the multi-degree-of-freedom support mechanism 5 can efficiently prevent the table 2a from flexing because of the short distance between the bed device 2 supporting one end of the table 2a and the table support portion 5a.

Moreover, although the description above assumes that the table 2a is moved by the bed 2, the following command may be given by the control device, for example. Specifically, the bed 2 moves the table 2a until the end of the table 2a is supported by the multi-degree-of-freedom support mechanism 5, and thereafter, the table 2a moves by being pulled by the multi-degree-of-freedom support mechanism 5. In this case, by forming the table support portion 5a into such a shape that can grip the table 2a or fit onto the table 2a as described above, the table 2a can be reliably moved without flexure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus comprising:
a bed configured to move a table on which an examinee lies down;
a gantry having a tunnel-shaped inner portion into which the bed moves and inserts the table with which the examinee is in direct contact, and being configured to obtain information on an interior of the examinee by imaging the examinee located in the inner portion;

a console configured to control drive of the bed and the gantry; and a multi-degree-of-freedom support mechanism installed at a position facing the bed with the gantry interposed between the multi-degree-of-freedom support mechanism and the bed, the multi-degree-of-freedom support mechanism including a table support configured to support the table by coming into direct contact with the table, a plurality of arms each positioned below the bed and configured to contact a bottom of the table to support the table to a position near the inner portion of the gantry and to support the table based on a control by the console in accordance with movement of the table by the bed, and connection portions between the plurality of arms configured to respectively connect each of the plurality of arms to be rotatable relative to an adjacent one of the plurality of arms.

2. The medical diagnostic imaging apparatus according to claim 1, wherein
the console instructs the bed to move the table toward the gantry, and then when the table reaches a predetermined position, the console instructs the multi-degree-of-freedom support mechanism, instead of the bed, to move the table.

3. The medical diagnostic imaging apparatus according to claim 1, wherein the multi-degree-of-freedom support mechanism is configured to be movable in a width direction of the gantry owing to the connection portions.

4. The medical diagnostic imaging apparatus according to claim 1,
wherein when a plurality of gantries are installed as wherein the gantry comprises more than one gantry and are each configured to be movable, the multi-degree-of-freedom support mechanism is installed between the gantries.

5. The medical diagnostic imaging apparatus according to claim 1, wherein when a plurality of gantries are installed as wherein the gantry comprises more than one gantry, the multi-degree-of-freedom support mechanism is installed at a position facing the bed with the multiple gantries interposed in between.

6. The medical diagnostic imaging apparatus according to claim 5, wherein
the console instructs the bed to move the table toward the gantry, and then when the table reaches a predetermined position, the console instructs the multi-degree-of-freedom support mechanism, instead of the bed, to move the table.

7. The medical diagnostic imaging apparatus according to claim 1, wherein when the table starts moving toward the gantry, the console controls the multi-degree-of-freedom support mechanism to move the table support to the position near the inner portion of the gantry to stand by for the table.

8. The medical diagnostic imaging apparatus according to claim 7, wherein
the console instructs the bed to move the table toward the gantry, and then when the table reaches a predetermined position, the console instructs the multi-degree-of-freedom support mechanism, instead of the bed, to move the table.

9. The medical diagnostic imaging apparatus according to claim 7, wherein the multi-degree-of-freedom support mechanism is configured to be movable in a width direction of the gantry owing to the connection portions.

10. The medical diagnostic imaging apparatus according to claim 7, wherein the multi-degree-of-freedom support mechanism comprises:
a first arm configured to movably support, at a first end, the table support;
a first connection portion being located at a second end of the first arm and configured to rotatably support the first arm;
a second arm connected at a first end to the first connection portion and thereby connected to the first arm;
a second connection portion being located at a second end of the second arm and configured to rotatably support the second arm;
a third arm connected at a first end to the second connection portion and thereby connected to the second arm;
a third connection portion being located at a second end of the third arm and configured to movably support the third arm; and
an installation portion configured to fix the multi-degree-of-freedom support mechanism to an installation surface.

11. The medical diagnostic imaging apparatus according to claim 10, wherein the table support of the multi-degree-of-freedom support mechanism is configured to be rotatable in a moving direction of the table.

12. The medical diagnostic imaging apparatus according to claim 10, wherein the table support of the multi-degree-of-freedom support mechanism is configured to be able to be fitted to the table.

13. The medical diagnostic imaging apparatus according to claim 10, wherein
the console instructs the bed to move the table toward the gantry, and then when the table reaches a predetermined position, the console instructs the multi-degree-of-freedom support mechanism, instead of the bed, to move the table.

14. The medical diagnostic imaging apparatus according to claim 10, wherein the multi-degree-of-freedom support mechanism is configured to be movable in a width direction of the gantry owing to the third connection portion.

15. The medical diagnostic imaging apparatus according to claim 1, wherein
the console is configured to, after moving the table support to the position near the inner portion or the gantry, keep the table support standing by at the position until the table moves to the position such that the multi-degree-of-freedom support mechanism supports the table when imaging starts after the table enters the inner portion.

16. The medical diagnostic imaging apparatus according to claim 15, wherein
the console instructs the bed to move the table toward the gantry, and then when the table reaches a predetermined position, the console instructs the multi-degree-of-freedom support mechanism, instead of the bed, to move the table.

17. The medical diagnostic imaging apparatus according to claim 15, wherein the multi-degree-of-freedom support mechanism is configured to be movable in a width direction of the gantry owing to the connection portions.

18. The medical diagnostic imaging apparatus according to claim 15, wherein
the multi-degree-of-freedom support mechanism comprises:
a first arm configured to movably support, at a first end, the table support;

a first connection portion being located at a second end of the first arm and configured to rotatably support the first arm;

a second arm connected at a first end to the first connection portion and thereby connected to the first arm;

a second connection portion being located at a second end of the second arm and configured to rotatably support the second arm;

a third arm connected at a first end to the second connection portion and thereby connected to the second arm;

a third connection portion being located at a second end of the third arm and configured to movably support the third arm; and an installation portion configured to fix the multi-degree-of-freedom support mechanism to an installation surface.

19. The medical diagnostic imaging apparatus according to claim 18, wherein the table support of the multi-degree-of-freedom support mechanism is configured to be rotatable in a moving direction of the table.

20. The medical diagnostic imaging apparatus according to claim 18, wherein the table support of the multi-degree-of-freedom support mechanism is configured to be able to be fitted to the table.

21. The medical diagnostic imaging apparatus according to claim 18, wherein the multi-degree-of-freedom support mechanism is configured to be movable in a width direction of the gantry owing to the third connection portion.

22. The medical diagnostic imaging apparatus according to claim 1, wherein
the multi-degree-of-freedom support mechanism comprises:
a first arm configured to movably support, at a first end, the table support;
a first connection portion being located at a second end of the first arm and configured to rotatably support the first arm;
a second arm connected at a first end to the first connection portion and thereby connected to the first arm;
a second connection portion being located at a second end of the second arm and configured to rotatably support the second arm;
a third arm connected at a first end to the second connection portion and thereby connected to the second arm;
a third connection portion being located at a second end of the third arm and configured to movably support the third arm; and
an installation portion configured to fix the multi-degree-of-freedom support mechanism to an installation surface.

23. The medical diagnostic imaging apparatus according to claim 22, wherein the multi-degree-of-freedom support mechanism is configured to be movable in a width direction of the gantry owing to the third connection portion.

24. The medical diagnostic imaging apparatus according to claim 22, wherein
the console instructs the bed to move the table toward the gantry, and then when the table reaches a predetermined position, the console instructs the multi-degree-of-freedom support mechanism, instead of the bed, to move the table.

25. The medical diagnostic imaging apparatus according to claim 22, wherein the table support of the multi-degree-of-freedom support mechanism is configured to be rotatable in a moving direction of the table.

26. The medical diagnostic imaging apparatus according to claim 25, wherein
the console instructs the bed to move the table toward the gantry, and then when the table reaches a predetermined position, the console instructs the multi-degree-of-freedom support mechanism, instead of the bed, to move the table.

27. The medical diagnostic imaging apparatus according to claim 22, wherein the table support of the multi-degree-of-freedom support mechanism is configured to be able to be fitted to the table.

28. The medical diagnostic imaging apparatus according to claim 27, wherein
the console instructs the bed to move the table toward the gantry, and then when the table reaches a predetermined position, the console instructs the multi-degree-of-freedom support mechanism, instead of the bed, to move the table.

* * * * *